United States Patent
Komaromi et al.

(10) Patent No.: US 9,990,172 B2
(45) Date of Patent: Jun. 5, 2018

(54) WEARABLE ELECTRONIC DEVICE

(71) Applicant: Sensirion AG, Stafa (CH)

(72) Inventors: Heiko Komaromi, Aathal-Seegräben (CH); Marcel Koller, Rapperswil (CH)

(73) Assignee: Sensirion AG, Stafa (CH)

( * ) Notice: Subject to any disclaimer, the term of this patent is extended or adjusted under 35 U.S.C. 154(b) by 0 days. days.

(21) Appl. No.: 14/943,489

(22) Filed: Nov. 17, 2015

(65) Prior Publication Data

US 2016/0162256 A1 Jun. 9, 2016

(30) Foreign Application Priority Data

Dec. 3, 2014 (EP) ..................... 14196042

(51) Int. Cl.
| | |
|---|---|
| *G06F 17/00* | (2006.01) |
| *G06F 3/16* | (2006.01) |
| *A61B 5/01* | (2006.01) |
| *A61B 5/145* | (2006.01) |
| *H04R 25/00* | (2006.01) |
| *H04M 1/725* | (2006.01) |
| *H04Q 9/00* | (2006.01) |
| *A61B 5/12* | (2006.01) |

(Continued)

(52) U.S. Cl.
CPC ............... *G06F 3/165* (2013.01); *A61B 5/01* (2013.01); *A61B 5/14517* (2013.01); *A61B 5/681* (2013.01); *A61B 5/6817* (2013.01); *H04M 1/72569* (2013.01); *H04Q 9/00* (2013.01); *H04R 1/1041* (2013.01); *H04R 25/305* (2013.01); *A61B 5/12* (2013.01); *A61B 5/4266* (2013.01); *A61B 2560/029* (2013.01); *A61B 2560/0252* (2013.01); *A61B 2560/0462* (2013.01); *A61B 2562/029* (2013.01); *A61B 2562/043* (2013.01); *A61B 2562/063* (2013.01); *H04R 1/1016* (2013.01); *H04R 2225/61* (2013.01)

(58) Field of Classification Search
CPC .................. A61B 5/681; A61B 5/6803; A63B 2071/0663; A63B 2071/0666; A63B 2230/50
See application file for complete search history.

(56) References Cited

U.S. PATENT DOCUMENTS

| | | |
|---|---|---|
| 8,838,037 B2 | 9/2014 | Niederberger et al. |
| 2002/0137992 A1 | 9/2002 | Lahtinen |
| 2006/0141945 A1 | 6/2006 | Korhonen et al. |
| 2006/0150714 A1 | 7/2006 | Imhof |
| 2006/0243048 A1 | 11/2006 | Imhof |
| 2007/0185392 A1 | 8/2007 | Sherman et al. |

(Continued)

FOREIGN PATENT DOCUMENTS

| | | |
|---|---|---|
| CN | 103002373 | 3/2013 |
| EP | 1921449 | 5/2008 |

(Continued)

OTHER PUBLICATIONS

Measuring Sweat Rate Using One or More Humidity Sensors, An IP.com Prior Art Database Technical Disclosure, Jan. 6, 2014.

*Primary Examiner* — Thomas Maung
(74) *Attorney, Agent, or Firm* — Cooper & Dunham LLP

(57) ABSTRACT

A wearable electronic device (100) comprises a sensor (1) providing a sensor signal (s1), which sensor (1) is one of a temperature sensor and a humidity sensor. A control unit (3) determines, subject to at least the sensor signal (s1), if the wearable electronic device (100) is worn by a user, and provides an output signal (t1) indicative of a result of the determination.

20 Claims, 3 Drawing Sheets

(51) Int. Cl.
  *A61B 5/00* (2006.01)
  *H04R 1/10* (2006.01)

(56) References Cited

U.S. PATENT DOCUMENTS

| | | |
|---|---|---|
| 2008/0012582 A1 | 1/2008 | Jang et al. |
| 2008/0044939 A1 | 2/2008 | Nassiopoulou et al. |
| 2008/0064413 A1 | 3/2008 | Breed |
| 2008/0216171 A1 | 9/2008 | Sano et al. |
| 2011/0213559 A1* | 9/2011 | Pollack ............... A61B 5/0008 702/19 |
| 2012/0029410 A1 | 2/2012 | Koenig et al. |
| 2012/0114156 A1 | 5/2012 | Serman et al. |
| 2012/0232421 A1 | 9/2012 | Jang et al. |
| 2013/0072765 A1* | 3/2013 | Kahn ....................... A61B 5/01 600/301 |
| 2014/0135631 A1* | 5/2014 | Brumback ......... A61B 5/02438 600/479 |
| 2014/0161412 A1* | 6/2014 | Chase ................ H04N 21/2743 386/224 |
| 2014/0321682 A1* | 10/2014 | Kofod-Hansen .... H04R 25/305 381/315 |

FOREIGN PATENT DOCUMENTS

| | | |
|---|---|---|
| EP | 2498481 | 9/2012 |
| JP | 2001093068 | 4/2001 |
| JP | 2005159724 | 6/2005 |
| JP | 2006098098 | 4/2006 |
| JP | 2010201138 | 9/2010 |
| WO | 2004066194 | 8/2004 |

\* cited by examiner

WEARABLE ELECTRONIC DEVICE

TECHNICAL FIELD

This application claims priority of European Patent Application 14196042.7, filed Dec. 3, 2014, the contents of which is incorporated herein by reference in its entirety.

The present invention relates to a wearable electronic device, and to a method for determining if a wearable electronic device is worn by a user.

BACKGROUND ART

Wearable electronic devices such as smart watches, for example, become ubiquitous these days.

DISCLOSURE OF THE INVENTION

According to a first aspect of the present invention, a wearable electronic device is introduced, comprising a sensor providing a sensor signal, which sensor is one of a temperature sensor and a humidity sensor, and a control unit configured to determine, subject to at least the sensor signal, if the wearable electronic device is worn by a user, and configured to provide an output signal indicative of a result of the determination.

The wearable electronic device, which may also be referred to as device in the following, may for example, be one of a hearing aid, an earphone, a headphone, a watch, glasses, goggles, a helmet, a shoe, a body-worn device such as a leg-worn device or a belt-worn device, a fitness wearable, a dedicated medical device, a safety device, a piece of clothing also referred to as smart cloth, etc. In a different embodiment, the wearable electronic device at least includes one of the above items as wearable unit and in addition may include a unit remote from the wearable unit which remote unit may be portable, for example, such as a smart phone or a tablet computer, or even may be a stationary device comprising computational capabilities.

The term wearable indicates that the device or the wearable unit thereof is suited to be attached to a part of a human body, most of the times to a designated part owed to a functionality and/or a shape of the device. For this purpose, the device or the wearable unit thereof may comprise dedicated attachment means such as a wristlet of a watch for attaching the watch to the wrist of a user, or earpieces of glasses for making the glasses rest on the nose of a user. However, other wearable electronic devices or units thereof may not show dedicated attachment means such as earphones, for example, which may be inserted in the auditory canal of a user solely based on their shape. Typically, a wearable electronic device is in touch with a body portion of the user or has at least a unit that is in touch with a body portion of a user while being worn. Some wearable devices require a direct contact to the body portion, for example, in case the wearable electronic device comprises a medical sensor that relies on a direct contact to the skin. Other wearable devices may be attached to a body portion of the user but may allow a textile layer between the wearable electronic device and the skin of the user.

The term electronic indicates, that the device makes use of a control unit that may be based on semiconductor electronics. Those devices are also labelled as "smart" devices these days given that the origin of the subject device often is a conventional device without any electronics. Such device in the past became enhanced by adding electronics for adding functionality. Examples may be so-called smart watches or smart glasses.

At least one sensor in form of a temperature or a humidity sensor is provided in, on or at the wearable electronic device for allowing a determination, if the wearable electronic device presently is worn by a user. In case the sensor is a temperature sensor, the sensor may be used for sensing the presence or absence of a temperature representative of a body temperature of the user. In case the sensor is a humidity sensor, the sensor may be used for sensing a trans-epidermal water-loss of the skin of the user or of sweat.

For this purpose, the sensor preferably is arranged at a location of the wearable device that allows sensing the above variables. In one embodiment, the location of the sensor, and preferably the sensor itself faces a body part of the user during the device being worn by the user. For example, in case of the device being a wristwatch, the temperature or humidity sensor may be arranged at a bottom side of a wristlet of the watch facing the wrist/arm of the user when the watch is strapped around the user's wrist, which faces the body part/skin of the user when the wristwatch is put on.

Hence, the sensor may be arranged in a housing of the device possibly together with the control unit, or be integrated in attachment means of the device or the wearable component for attaching the device/component to the body of the user. Typically, it is preferred that the sensor indeed faces the skin of the user while the wearable electronic device is worn. Facing in this context, however, does not require an exact arrangement of the sensor opposite the skin. Any arrangement that sufficiently exposes the sensor to the variable to be measured, e.g. the body temperature, the sweat of the trans-epidermal water loss shall be deemed to face the subject body portion. Hence, the sensor may also be arranged in a cavity of the housing with an opening of the cavity facing the body during wearing. In another alternative, the sensor may even be embedded in the device and/or its attachment means as long as a sufficient access is granted for the variable to measure. For example, in case the sensor is a temperature sensor, the sensor may be embedded in the wristlet, however, in a bottom side thereof that faces the body portion. Such location may still be sufficient for sensing the body temperature, as long as a material of the wristlet is of a sufficient thermal conductance. Summarizing, it is not necessarily the sensor itself that faces the body part, as long as the location provides sufficient access to the body part when the device is worn. In other words, the location of the sensor is chosen to show different values in the variable between a first state in which the device is worn by the user and a second state in which the device is not worn by the user.

A signal of the sensor is evaluated by a control unit. Dependent on the signal, or dependent on several sensor signals in case of several sensors provided for detecting if the device is presently worn, the control unit determines if the wearable electronic device presently is worn by a user. The one or more signals may be evaluated as to one or more of its/their absolute value, as to its/their value relative to the value of another sensor as will be explained later on, as to its/their change in first or second or higher order, as to the presence of a predefined pattern, etc.

In one embodiment, this evaluation permanently runs as a background process during the device being powered. In a different embodiment, this evaluation may run also in case the device is presently not powered wherein the evaluation may be powered by a separate energy storage, or an emergency power source.

As a result of the evaluation, the control unit may supply an internal or external output signal at least indicative if the device/the wearable component presently is worn, or is not worn. Hence, in one embodiment the output signal is a binary signal. In a different embodiment, the output signal may take multiple levels and indicate additional information as to a wearing status of the device.

It is preferred, that the output signal is used to automatically trigger an action of/on/in the wearable electronic device. In case of a binary output signal, the signal states itself may trigger an action, and/or a change between signal states may trigger an action.

The action triggered is subject to the kind of wearable electronic device. However, for any wearable electronic device, one action may be to either power down or to switch to a stand-by mode if the output signal changes from a detected "on-body" state—i.e. the device is worn by a user—to an "off-body" state—i.e. the device is detected to no longer be worn. This action may support saving battery power which is important for wearable devices of all kind in view of a lack of a permanent power source. Hence, in one example, a hearing aid may be powered down when the hearing aid is determined to be—off-body—i.e. out of the ear of the user. The same may hold for earphones. Also glasses, watches, headphones or clothes with integrated electronics may no longer be supported by power in case an off-body state is detected. As said before, the action may be triggered in response to a change of the value of the output signal, or may be connected to presence of a state of the output signal.

The action may also include repowering the device or returning from a stand-by mode into an active mode at a time the device is detected to be on-body again.

For all the above embodiments referring to the power management of the wearable electronic device, instead of controlling the power of the entire device, the powering of one or more components, and in particular hardware components, such as a display, a wireless transceiver, a sensor hub, can automatically be controlled dependent on the output signal. The same concept can be applied to apps/applications or software modules in general, which may be activated or deactivated subject to the output signal.

For example, in the case of earphones as wearable component, a music player of a remote device—such as a dedicated MP3 player or a smartphone the earphones are connected to—preferably is stopped in case the earphones are detected to no longer be worn in the users ear/s. On the other hand, a music player of the remote device and possibly the entire remote device is prevented from being powered down as long as the earphones are detected to be worn. Or, in case the earphones are presently used for calling, the call may be stopped as soon as the earphones are detected to no longer be in the user's ears.

In another embodiment, the device is a wrist watch or another device, including a dedicated device, for monitoring a medical variable of the user, such as blood pressure, heart rate, etc. Corresponding sensors for performing these measurements may be activated or de-activated subject to the output signal. However, another action may rather impact a logging of such sensor data which may be stopped in response to the device being detected to be off-body. Again, energy resources can be saved.

Generally, it may be preferred to switch off one or more of the device, a component, a process, an app in case the device is detected to be off-body, while in another embodiment it is preferred to switch on or continue to power one or more of the device, a component, a process, an apps etc. in case the device is detected to be on-body.

The device may comprise one or more sensors for performing the on-body detection. In case of several sensors, all sensors may be of the same type, i.e. all sensors may be temperature sensors, or all sensors may be humidity sensors, while in different embodiment, at least one sensor may be a temperature sensor while another sensor may be a humidity sensor.

The following arrangements of one or more sensors are especially preferred:

A single temperature sensor is provided for the purpose of on-body detection. This does not exclude the presence of other temperature sensors in the device for other purposes, e.g. for monitoring the temperature of a processing unit. In case of a single temperature sensor, it is preferred that this temperature sensor is arranged at a location of the device that senses a body temperature in case the device is worn by a user. In one embodiment, the device may be detected to be worn in case the temperature sensed is around 37° Celsius as typical body temperature of humans. The presence of a possible environmental temperature which would result in a false positive may be excluded by, for example, by evaluating not only the temperature level but also the dynamics of the temperature signal. In case a sudden rise in temperature is detected prior to reaching the temperature of 37° Celsius, it can safely be assumed to have detected a device that previously was not worn but now is worn, in view of the environmental temperature not rising such at such a speed. On the other hand, in case a temperature is detected that is outside the temperature range defined as typical for a human body temperature, it can safely be assumed that the device presently is not worn by a user. In a different embodiment, a single humidity sensor is provided for the purpose of on-body detection. In case of a single humidity sensor, it is preferred that this humidity sensor is arranged at a location of the device that senses a humidity released by the skin of the user, which can be trans-epidermal water loss or sweat, which can be detected when the humidity sensor is arranged at a suitable location of the device. A range for a typical on-body humidity may be defined upfront, and when such humidity range is met by the humidity signal, the device can be classified to be worn. The presence of a possible environmental humidity which would result in a false positive may be excluded, for example, by evaluating not only the humidity level but also the dynamics in the humidity signal. In case a sudden rise in humidity is detected prior to reaching the humidity range representative for the presence of a human, it can safely be assumed that the device previously was not worn but now is worn, in view of the environmental humidity typically not rising at such speed. On the other hand, in case the sensed humidity is outside the humidity range defined as typical for a human, it can safely be assumed that the device presently is not worn by a user.

In the embodiment of a further sensor being provided and the further sensor being of the same type as the sensor, different arrangements and evaluations can be applied for enhancing the reliability of the evaluation. Preferably, the other sensor is arranged at a location of the wearable electronic device at which location the other sensor is supposed to sense a value different to the sensor during wearing the device, and in particular to sense an ambient temperature value or an ambient humidity value in a state in which the wearable electronic device is worn by the user.

In one example, the sensor is a temperature sensor and is arranged at a location of the device facing the body part of the user during the device being worn. Under the assumption that the other sensor is also a temperature sensor, the other sensor is arranged at a location of the device that is sufficiently exposed to ambient air during the device being worn. As such, the other temperature sensor detects a temperature of the ambient air irrespective if the device presently is on-body or off-body. In the example of the wrist watch, the first temperature sensor may be arranged at a bottom side of the watch housing while the other temperature sensor is arranged opposite at a top side of the watch housing and faces the ambient even during wearing the device. Hence, a comparison of the temperature values sensed by first and the other temperature sensor can allow for a discrimination between an on-body state and an off body state of the device. In case both temperature signals show a comparable temperature value, it can be assumed that the device presently is not worn. However, in case the signals show different values, and preferably wherein in addition the sensor for detecting the body temperature shows a value in the range defined as plausible for a body temperature, an on-body state is determined. For avoiding false positives, again, a change of the signals over time can be evaluated. In case both signals rise slowly to the temperature range indicative of a body temperature, it can be assumed that the device is off-body in an environment where the ambient temperature rises. Instead, in case the first temperature signal rises quickly while the other temperature signal rises slowly, it can be assumed that at the time the first temperature signal has risen quickly the device was put on by a user.

In the case of two temperature sensors and the above sensing concept, it is preferred that the temperature sensors are arranged at locations of the wearable electronic device being sufficiently thermally decoupled from each other. This ensures that, for example, the temperature sensed by the other temperature sensor does not originate from the human body and migrates to the other temperature sensor through the housing of the device.

All what is said with respect to the arrangement of two temperature sensors applies to the arrangement of two humidity sensor in analogue fashion. Hence, while the first humidity sensor is arranged facing the body portion during wearing, the other humidity sensor is arranged at a location of the device to sense an ambient humidity even if the device is worn by the user. Preferably, the humidity sensor sense the humidity in different air volumes, and preferably, the two humidity sensors are arranged at opposite sides of the device. The evaluation by the control unit makes use of the first humidity signal and the second humidity signal in ways corresponding to the evaluation of the two temperature signals referred to above.

However, in a different embodiment, the two humidity sensors do not sense different air volumes but sense an air volume propagated in a common channel. Hence, it is preferred that the two humidity sensors are arranged in this channel which channel has at least one opening. This opening is arranged at a location of the wearable electronic device facing a body part of a user during wearing. Preferably, the channel has another opening that is arranged at a location of the device not facing the body portion, e.g. on an opposite side of the device. The first humidity sensor is arranged at a first distance from the opening, and the other humidity sensor is arranged at a second distance from the opening exceeding the first distance. Hence, the humidity sensors are arranged in series in the channel. The sensor and the other sensor preferably are arranged on a preferably common circuit board According to a second aspect of the present invention, a wearable electronic device comprises a sensor providing a sensor signal, which sensor is one of a temperature sensor and a humidity sensor, and another sensor providing another sensor signal, which other sensor is one of a temperature sensor and a humidity sensor. The device further comprises a channel ending in at least one opening to the outside. The opening is arranged at a location of the device facing a body part of a user during wearing the device. The sensor is arranged in the channel at a first distance from the opening and the other sensor is arranged at a second distance from the opening which first distance is less than the second distance. The sensor and the other sensor are arranged on a preferably common circuit board.

In the aspects and embodiments comprising at least two sensors arranged in spatial series in a channel of the device, the following measurements may be taken. In a first embodiment, the sensor and the other sensor are both humidity sensors sensing relative humidity. Hence, by subtracting the other sensor signal from the sensor signal, a relative humidity flux can be determined. In a second embodiment, the sensor and the other sensor are both temperature sensors. Hence, by subtracting the other sensor signal from the sensor signal, a heat flux can be determined which may be a measure for a trans-epidermal water loss the user experiences. In a third embodiment, the sensor and the other sensor are both humidity sensors sensing absolute humidity. Hence, by subtracting the other sensor signal from the first sensor signal, a relative absolute flux can be determined which is also referred to as sweat rate since it is provides a measure as to the amount of sweat the user produces. However, the three embodiments can also be combined. In a preferred combination, two humidity sensors sensing relative humidity each and two temperature sensors are provided. By means of such arrangement, the sweat rate can be determined, too, since the absolute humidity can be calculated from the relative humidity and the temperature as is known in the art.

Generally, each of the above flux rates—including the sweat rate—may be used for determining, if the device or at least its wearable component is presently worn, e.g. in case such flux rate exceeds a threshold and as such indicates that a body part is present in front of the opening which body part radiates heat or humidity into the channel. However, in a different approach, each of the above flux rates—including the sweat rate—may also be used for different purposes, e.g. for displaying the subject flux rate to a user wearing the device. This may in particular be beneficial in case the sensor arrangement is provided in a fitness wearable, for example, such that the user receives feedback about his/her sweating activity. In this approach, the control unit provides a signal indicative of the flux rate determined. Of course, both output signals, one referring to the flux rate and the other one indicative of the device is worn can be provided by the control unit.

Preferably, the channel includes the shape of an "S", or an "L". In a different embodiment, the channel is straight.

In a preferred embodiment, the circuit board—e.g. a printed circuit board or a flexible printed circuit board—is sandwiched between a first housing part and a second housing part of the device. Preferably, in such configuration at least a portion of the channel is formed by a recess in one of the first and the second housing part. At least a portion of the circuit board containing the two sensors faces the recess such that the two sensor are arranged in the channel. Preferably, in case the first and the second housing parts take the shape of plates with the flat circuit board clamped in between, both plates may provide a through-hole defining an inlet and an outlet to the channel and as such defining the opening and the other opening. The circuit board may comprise a through-hole, too, for connecting the inlet with the outlet. In such arrangement, a seal may be provided on each side of the circuit board to seal the channel against an interior of the housing. Such arrangement may result in an "S"-form of the channel.

In a very preferred embodiment, the channel is arranged in an earphone, preferably horizontally, i.e. orthogonal to an outlet of the earphone for a wire connecting to the audio player such as an MPx player, a smart phone, a tablet, etc. The earphone may additionally comprise the control unit. Alternatively, the control unit may be arranged in a unit remote from the earphone to which the earphone is electrically connected. In the control unit, it can be determined, if the earphone is presently worn by a user, i.e. if it inserted into the ear, or not. The flux rate that calculated from the sensor signals of the two sensors is used for this determination. This information may be used for triggering one or more actions by the control unit.

Generally, an action to be triggered may include powering on or powering off one or more of the device, a hardware component thereof, and/or a software application thereof. Instead of powering on or off, the device, the component or the application may be switched on or switched off from/in a stand-by mode, which is considered a low power mode and at least consuming less power than an active mode. These measures support saving power in view of the assumption that when a wearable device is not worn it does not necessarily be in a full active mode.

In a different embodiment, the device comprises one or more further sensors which may, for example, be medical sensors. One or more of powering the sensor/s, evaluating, or logging of data from the further sensor/s preferably is stopped or paused in response to the device no longer being detected to be worn.

In case the device comprises an earphone or a headphone, the output signal or the signal of the control unit may trigger pausing or stopping an active audio component or application that presently runs on the device. E.g., music is played and output via earphones or the headphone. However, in case the earphone/s or a headphone is detected not to be worn, playing music may be useless such that the control unit pauses or stops the playing of the audio. This saves energy which in particular is important in mobile devices. Preferably, the control unit and the audio component—e.g. an audio player—or application are provided in a smartphone or the like as a remote unit the earphone/s or the headphone is connected to.

The same concept may be applied to videos. In this instance, the device may comprise glasses or a watch with the capability of playing a video. The output signal or the signal of the control unit may trigger pausing or stopping an active video component or application that presently runs on the device. The control unit preferably is integrated in the glasses or watch. Alternatively, the control unit and the video component—e.g. a video player—or application may be provided in a smartphone or the like as a remote unit the glasses or the watch is connected to.

The video may represent an augmentation in an augmented reality application, or may represent a virtual reality in a virtual reality application.

In the case of a pair of earphones is connected to a remote unit such as a smartphone, only a single earphone of the pair may be provided with a sensor for detecting wearing of the device, or both. In the case of both earphones of the pair being equipped with a sensor arrangement, the control unit may receive two output signals and only trigger the respective action in case both output signals show an unworn state for the pair of earphones.

In a different embodiment, a microphone, preferably of a remote unit of the device—e.g. a microphone of a smartphone connected to the earphones or the headphone as a wearable unit—is muted in response to the detection that the earphone or the headphone is taken off by the user. In particular, this action is taken only if in addition a phone call is active at the remote unit. When a user lifts the headphone or unplugs the earphones while calling, the mute control of the microphone may keep privacy in that it is assumed that the user temporarily disengages from the call, e.g. in order to discuss with other persons while not wanting to be heard over the phone. Preferably, the microphone may be unmuted again as soon as the earphones/headphone is detected to be worn again.

A different action in response to taking off one of earphones, a headphone, glasses or a watch may be to switch an active audio or video component or application respectively to a different audio or video output. In case the wearable unit is an earphone or a headphone that is connected to a remote unit, the audio output may be—in response to the wearable unit being taken off—switched from the earphone or headphone to a speaker in the remote unit, e.g. the speaker of a smartphone. In case of the wearable unit is smart glasses or a smart watch that is connected to a remote unit, the video output may be—in response to the wearable unit being taken off—switched from the glasses or watch to a display in the remote unit, e.g. the display of a smartphone.

In a different embodiment, the device comprises a wearable unit including one of an earphone and a headphone, and a remote unit e.g. in form of a smartphone. The control unit preferably is configured to—in response to detecting the earphone or the headphone being worn by a user and receiving a call by the smartphone—automatically switch the audio output of the call from the speaker in the smartphone to the earphone or the headphone respectively.

In another embodiment, the device comprises a wearable unit, for example including one of an earphone, a headphone, a smart watch, smart glasses, etc., and a remote unit e.g. in form of a smartphone. The control unit which preferably resides in remote unit, preferably is configured to maintain the remote unit unlocked as long as the wearable unit is detected to be worn by a user. The control unit preferably is configured to lock the remote unit in response to the wearable unit being detected to no longer being worn by the user.

In a different embodiment, the device is or comprises a safety or a medical wearable unit wherein it is desired to monitor if such unit becomes disconnected from the users body. This, for instance, may be desirable for wearable units such as an infusion, a patch, a mask, a monitoring electrode, etc. Here, the control unit preferably is configured to generate an alert, e.g. an audible or visual alert, in case the result of the determination is that the safety or medical unit no longer is worn by the user.

In a preferred embodiment, the control unit is configured to log a change of states from "wear" to "not wear" and vice versa. By doing so, statistical information can be calculated for how long, for instance, the device is worn.

In the case of smart clothes, the wearable unit may, for example, be a tag built into the cloth. By evaluating the times of the cloth being worn or not worn, statistics can be provided.

Generally, and for the any of the above concepts including two sensors, reliability of the evaluation can be enhanced, if a temperature sensor is added to each location with a humidity sensor already present, and vice versa. Here, preferably four sensors are used and the signals of the fours sensors are evaluated for determining if a user wears a device or not. Plausibility checks can be run between the sensor signals stemming from sensors sensing different physical variables.

According to another aspect of the present invention, a method is provided for determining if a wearable electronic device is worn by a user. A temperature or a humidity is sensed by a temperature sensor or a humidity sensor respectively. Subject to at least the sensed temperature or the sensed humidity respectively, it is determined if the wearable electronic device is worn by the user. An output signal indicative of a result of the determination is provided.

According to a further aspect of the present invention, a method is provided for determining if a wearable electronic device is worn by a user. A first temperature or a first humidity is sensed by a temperature sensor or a humidity sensor respectively arranged in a channel at a first location at a first distance from an opening of the channel which opening faces a body part of a user during wearing the device. A second temperature or a second humidity is sensed by a second temperature sensor or a second humidity sensor respectively arranged in the channel at a second location at a second distance from the opening of the channel which first distance is less than the second distance, and is arranged together with the first temperature sensor or humidity sensor respectively on a—preferably common—circuit board.

Preferably, subject to at least the sensed temperatures or the sensed humidities respectively, a flux is determined. A signal indicative of a result of the determination is provided. In another embodiment, it is determined from the signal representing the flux if the wearable electronic device is worn by the user. An output signal indicative of a result of this determination is provided. Actions can be triggered in response to one or both of the signal and the output signal.

As a result, a wearable device is introduced that includes one of the following advantages: Power consumption is saved. Usability is enhanced. Convenience of use is enhanced, Functionality is enhanced.

Other advantageous embodiments are listed in the dependent claims as well as in the description below.

BRIEF DESCRIPTION OF THE DRAWINGS

Embodiments of the present invention and advantages are described in the detailed description following. Such description makes reference to the annexed drawings, wherein the figures show.

DETAILED DESCRIPTION OF THE DRAWINGS

Figure 1:
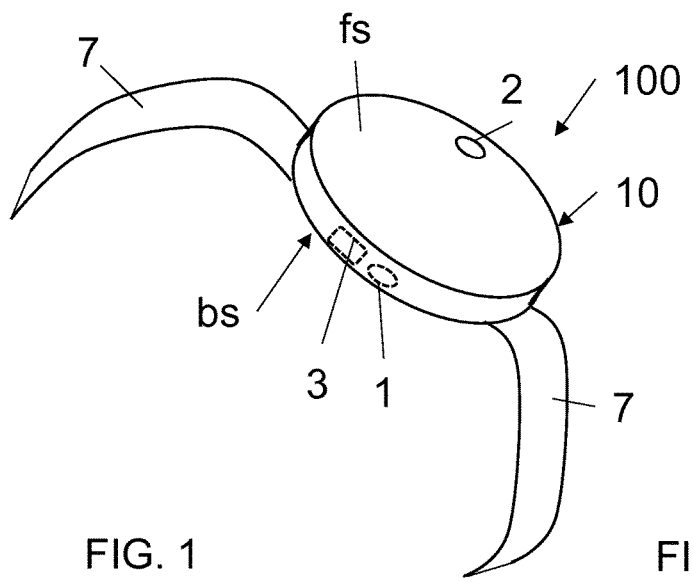
FIG. 1 a perspective schematic view on a smart watch as a wearable electronic device according to an embodiment of the present invention.

FIG. 1 illustrates a perspective schematic view on a smart watch as a wearable electronic device 100 according to an embodiment of the present invention. The smart watch comprises a housing 10 and attachment means 7 in form of wristlets for fixing the smart watch to the wrist of a user. A back side bs of the housing 10 is the side that faces the body part/wrist/skin of the user during wearing. A front side fs of the housing may show a display, a touchscreen if available and/or other input and/or output means (all not shown). A sensor 1 is arranged at the back side bs of the housing 10. For example, the sensor 1 is a temperature sensor and is arranged such that it has a good thermal contact to the body part of the user when wearing the smart watch. A control unit 3 is indicated in an interior of the housing 10 for processing a signal of the sensor 1. The control unit 3—which may be a processing unit of the smart watch that takes on control of many functions of the device—evaluates the sensor signal and provides an output signal for controlling one or more actuators dependent on a state of the output signal. The output signal can take, for example, two states, a first one representing the device being worn, and a second one representing the device not being worn.

Optionally, another sensor 2 in form of a temperature sensor may be arranged at the front side fs of the housing 10 of the smart watch. It is assumed that the other sensor 2 is thermally decoupled from the sensor 1 as far as possible, such that when the smart watch is worn, the other sensor 2 senses a temperature of the ambient rather than a body temperature of the user. This is owed to the deliberately chosen locations for the sensors 1 and 2. The other sensor 2 is connected to the control unit 3, too, and the other signal is evaluated, too, and preferably evaluated with respect to the sensor signal from the sensor 1. Hence, when the sensor 1 senses a value that may represent a body temperature while the other sensor 2 senses a temperature different from the value sensed by the sensor 1, it can be assumed that the smart watch presently is worn by a user.

In a different embodiment, the sensor 1, and optionally the other sensor 2, may be humidity sensors, wherein the sensor 1 senses a trans-epidermal water loss and/or sweat through the users skin when the smart watch is worn while the other sensor 2 in the same situation senses a humidity of the ambient.

Figure 2:
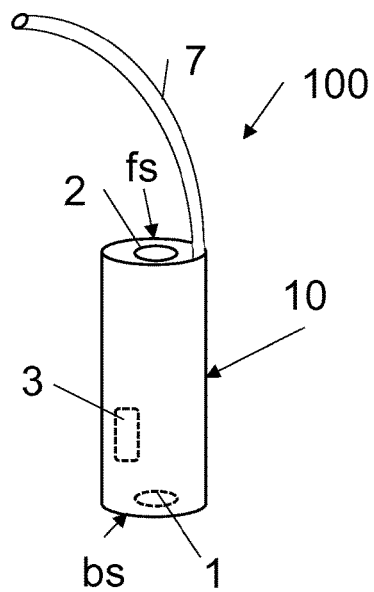
FIG. 2 a perspective schematic view of a hearing aid as a wearable electronic device according to an embodiment of the present invention.

FIG. 2 illustrates a perspective schematic view on a hearing aid as a wearable electronic device 100 according to an embodiment of the present invention. A housing 10 of the hearing aid has a front side fs and a back side bs and a bracket 7. The hearing aid is inserted in a user's ear with its back side bs ahead. A position of the hearing aid in the ear is fixed by means of the bracket 7. A control unit 3, also used for processing hearing aid functions, may receive signals from a sensor 1 arranged at the back side bs of the housing 10 such this sensor 1 faces a part of the outer hearing channel during wearing the device 100. The other sensor 2 instead is assumed to sense ambient temperature even during a user wearing this device. The other sensor 2 may instead face the environment while the device 100 is worn. The sensors 1 and 2 may temperature sensors, or be humidity sensors, and the sensor signals may be evaluated in the control unit 3.

Figure 3:
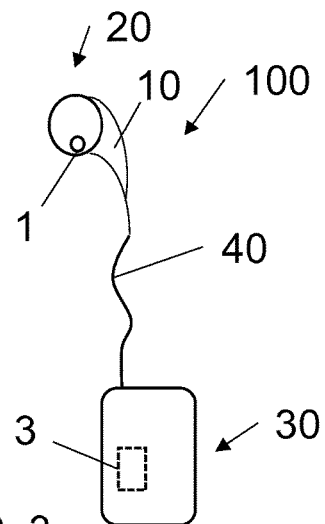
FIG. 3 a perspective schematic view of an earphones connected to a mobile phone collectively referred to as a wearable electronic device according to an embodiment of the present invention.

FIG. 3 illustrates a perspective schematic view of an earphone representing a wearable component 20 of a wearable electronic device 100 that is connected by a wired interface 40 to a remote unit 30 such as a smart phone, collectively referred to as a wearable electronic device according to an embodiment of the present invention. A sensor 1 is arranged at a housing or a membrane of the earphone. A signal of the sensor 1 is evaluated remote by a control unit 3 in the remote unit 30.

Figure 4:
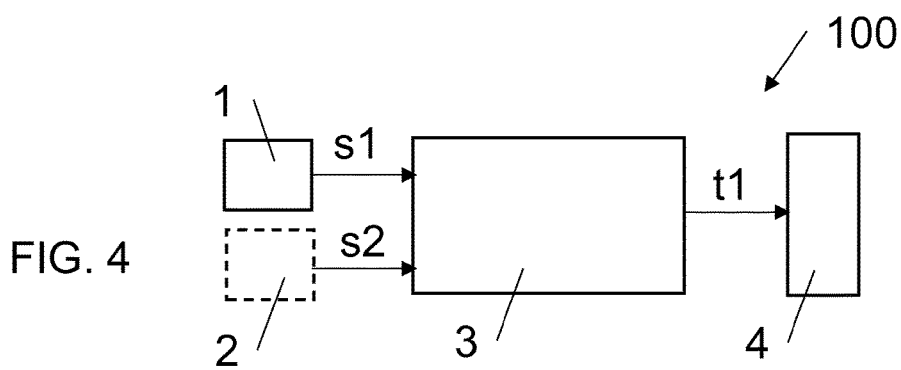
FIG. 4 a block diagram of a wearable electronic device according to an embodiment of the present invention.

FIG. 4 illustrates a block diagram of a wearable electronic device 100 according to an embodiment of the present invention. A sensor 1, and optionally another sensor 2 provide sensor signals s1 and s2 to a control unit 3. The control unit 3 evaluates the sensor signal/s s1 and possibly s2, and as a result of the evaluation provides an output signal tl which indicates if the device is worn by a user. Here, it is assumed that the control unit 3 is part of the component of the wearable electronic device that is worn. The output signal t1 may be received by an actuator 4, such as a display, for example. Hence, the output signal t1 may control the display such that when the output signal t1 indicates an on-body state of the device the display is powered on or remains active while when the output signal indicates an off-body state of the device, the display is powered off or remains inactive.

Figure 5:
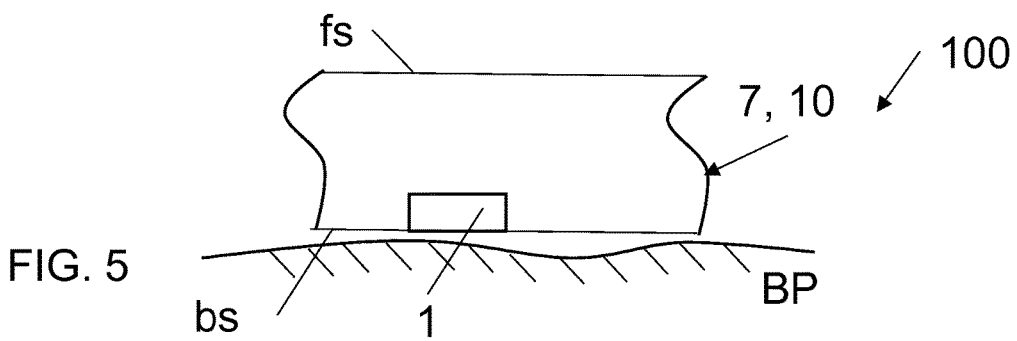
FIG. 5 a cut through a wearable electronic device according to an embodiment of the present invention.

FIG. 5 illustrates a cut through a portion of an attachment means 7 or a housing 10 of a wearable electronic device 100 according to an embodiment of the present invention. In one example, the attachment means 7 may be a wristlet of a watch. It is assumed that the device is presently worn by a user and touches or is in close proximity to a body part BP of the user. At a back side bs of the attachment means 7/or the housing 10 respectively, a sensor 1 is provided, that may be one of a temperature sensor or a humidity sensor. A signal of the sensor 1 is supplied to a control unit not shown which may be in one of the attachment means 7 or, more preferably, in the housing 10.

Figure 6:
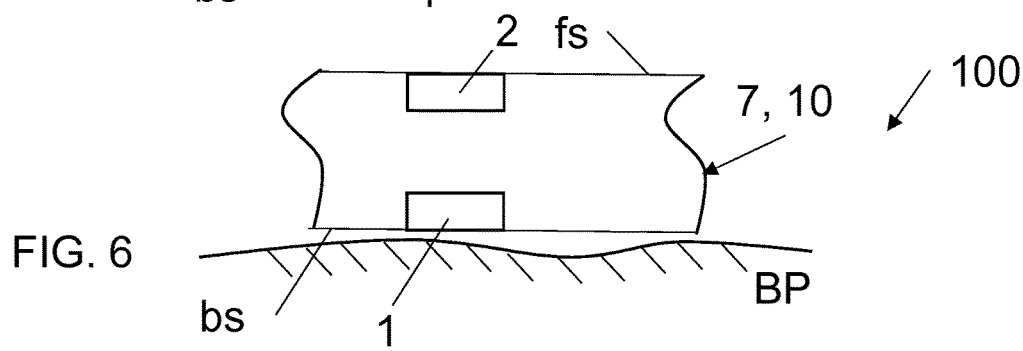
FIG. 6 a cut through another wearable electronic device according to an embodiment of the present invention.

FIG. 6 illustrates a cut through a portion of an attachment means 7 or a housing 10 of a wearable electronic device 100 according to another embodiment of the present invention. The embodiment of FIG. 6 is similar to the embodiment of FIG. 5, except that there is another sensor 2 provided at a location at a front side fs of the attachment means 7 or the housing 10 respectively. As can derived from FIG. 6, the other sensor 2 is arranged such that it senses an ambient temperature or an ambient humidity respectively rather the body temperature or the trans-epidermal water loss such as the sensor 1. In this context, it is preferred that in case the sensors 1 and 2 are temperature sensors there are no or only low thermally conducting connections between the sensor 1 and the other sensor 2, i.e. the sensors 1 and 2 are thermally decoupled as far as possible. In case the sensors 1 and 2 are humidity sensors, the bare choice of locations preferably grants that the other sensor 2 does not sense the same air volume as the sensor 1 which air volume is modulated by the trans-epidermal water loss. Hence, it is preferred in this embodiment that there is no channel provided between the sensor 1 and the other sensor 2.

Figure 7:
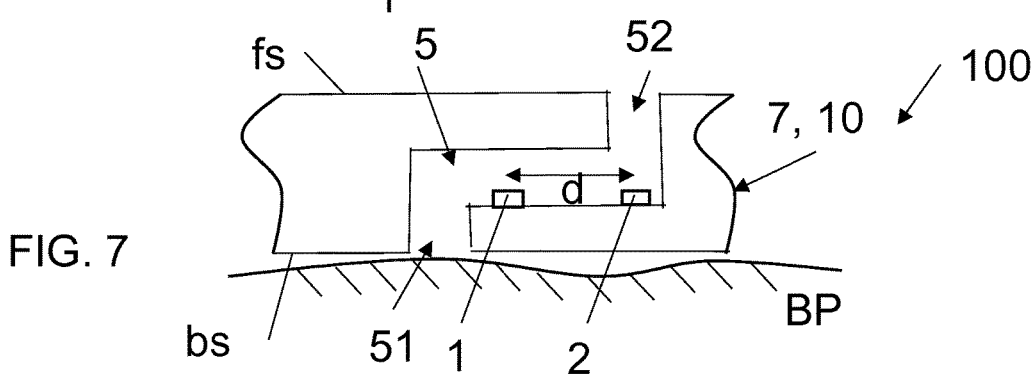
FIG. 7 a cut through a further wearable electronic device according to an embodiment of the present invention.

However, this feature is different in the embodiment of FIG. 7: Here, a channel 5 reaches through the attachment means 7 or the housing 10 respectively. The channel 5 has two openings 51 and 52, the first opening 51 facing a body part BP of the user when the device 100 is worn, the other opening 52 facing the environment. In the channel 5, the two sensors 1 and 2 are arranged. In a first embodiment, both sensors 1 and 2 are humidity sensors sensing absolute humidity, which are arranged such that a flux of vapour in the form of sweat that escapes from the users body part BP can be sensed by at the two different locations of the sensors 1 and 2. If the device is worn by a user, the sensor 1 will see an increased absolute humidity level than the other sensor 2 which difference may serve as an indicator that the device is worn by a user. Hence, a sweat rate of the user can be sensed which is kept alive as long as the opening 51 faces the body part BP. In contrast, in the device 100 is not worn, ambient air enters the channel 5 from both ends, and no sweat rate should be detectable. Accordingly, the device 100 can be classified as not being worn. A discrimination can be made by means of a threshold.

The sweat rate SR is calculated as follows:

$$SR = \alpha^*(s1-s2)/(d^*t)$$

wherein s1 is the sensor signal of the first sensor 1 representing absolute humidity values, s2 is the other sensor signal of the other sensor 2 representing absolute humidity values, α is a constant, d is a distance between the sensor 1 and the other sensor 2, and t is time.

Hence, the sweat rate is determined by a difference between the absolute humidity values s1 and s2 measured, divided by their distance, for a defined time t during which the measurement is taken. The result is dimensioned in $[g/(m^2*h)]$.

The distance between the sensors 1 and 2 preferably is in the range of [1 mm . . . 4 mm].

The channel 5 can have other shapes, and the sensors 1 and 2 may be arranged on a circuit board not shown which may be fixed in the channel 5 to the housing 10.

Instead of the sensors 1 and 2 measuring absolute humidity, the sensors 1 and 2 may both be temperature sensors. The calculation corresponds to the above formula with sensor signals s1 and s2 being temperature signals. The result of the determination is a heat flux.

Instead of the sensors 1 and 2 measuring absolute humidity, the sensors 1 and 2 may also measure relative humidity. The calculation corresponds to the above formula with sensor signals s1 and s2 being relative humidity signals. The result of the determination is a relative humidity flux.

Hence, a sensing arrangement is provided that senses a flux of one or more of humidity, temperature or sweat. A control unit may evaluate sensor signals of the two sensors 1 and 2, and provide the flux as signal t2, or may derive from the signal t2, e.g. by comparing to a threshold, if the flux is sufficient to stem from a human body part facing the opening 51. The unit shown in FIG. 7 may be a wearable device, or a wearable unit electrically connected to a remote unit. Preferably, the control unit is assigned to the wearable device, or to the remote unit if applicable, and may perform the corresponding calculations and/or evaluations.

The addition of a temperature sensor to each humidity sensor or vice versa may be preferred in all of the above embodiments. Then, two different measuring principles are applied at the same location which enhances reliability of the measuring results. Hence, in some embodiments, the control unit may receive four sensor signals from four sensors, i.e. from two humidity sensors and two temperature sensors. The control unit may determine dependent on these four sensor signals if the device is worn or not.

Figure 8:
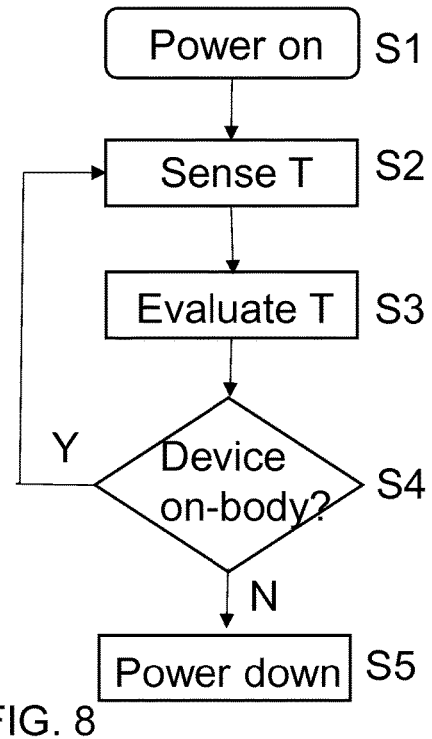
FIG. 8 a flow chart illustrating a method for determining if a wearable electronic device is worn by a user according to an embodiment of the present invention.

FIG. 8 shows a flow chart of a method for determining if a wearable electronic device is worn by a user according to an embodiment of the present invention. In step S1 it is assumed that the device is powered on which at the same time initiates the on-body/off-body detection, and, in case a single temperature sensor is provided for doing so, a measurement value T is taken in step S2. T is then evaluated in step S3, and in step S4 a determination is taken subject to the evaluation in step S3 if the device is detected to be on-body. If so (Y) it is returned to the temperature sensing step S2 and the process is repeated. However, in case it is detected in step S4 that the device is likely not to be arranged on a body part of a user (N), i.e. it is not worn, the device is powered down in step S5 for saving energy.

Figure 9:
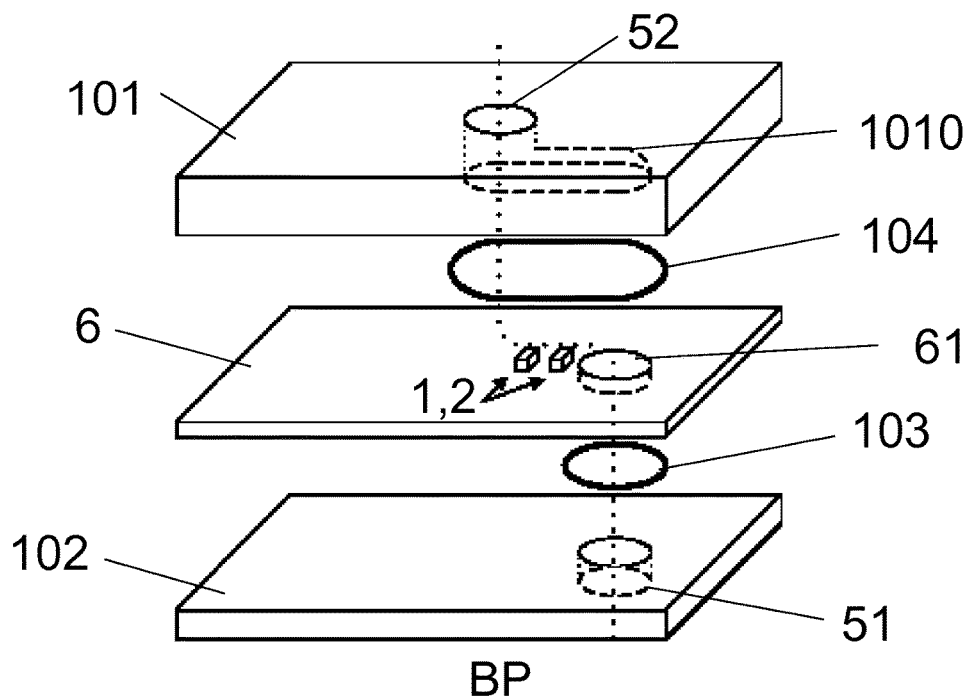
FIG. 9 a perspective schematic view of a wearable electronic device or a part of, according to an embodiment of the present invention.

FIG. 9 a perspective schematic view of a wearable electronic device or a part of, according to an embodiment of the present invention. This device resembles the device shown in FIG. 7 and therefore makes use of a channel. However, the way the channel is built is different from the embodiment of FIG. 7: While in FIG. 7, the sensor 1 and the other sensor 2 are arranged on parts of the housing 10 in the channel 5, in the present embodiment, the sensor 1 and the other sensor 2 are arranged on a circuit board 6, preferably a printed circuit board. The circuit board 6 is arranged between a first housing part 101 and a second housing part 102. Each housing part 101, 102 comprises a through-hole, however at different locations. The through-holes represent the opening 51 and the other opening 52 of the channel to be built when clamping the housing parts 101 and 102 and the circuit board 6 together. For providing access to the opening 51, a through-hole is provided in the circuit board 6, preferably at the same location as in the second housing part 102. Specifically, the sensors 1 and 2 are arranged in an area of the circuit board 6 connecting the opening 51 with the other opening 52. A recess 1010 is provided in the first housing part 101 facing the circuit board 6 and connecting to the opening 52. Now, by clamping together the housing parts 101 and 102 and the circuit board 6 in between, a channel is generated reaching from the opening 51, which is faced by a body part BP during application, through the circuit board 6, via the recess 1010, i.e. across the sensors 1 and 2, to the second opening 52. Seals 103 and 104 may be applied for sealing the channel versus an interior of the housing.

Hence, a sensing arrangement is provided that senses a flux of one or more of humidity, temperature or sweat. A control unit may evaluate sensor signals of the two sensors 1 and 2, and provide the flux as signal, or may derive from the flux, e.g. by comparing to a threshold, if the flux is sufficient to stem from a human body part BP facing the opening 51. The unit shown in FIG. 9 may be a wearable device, or a wearable unit electrically connected to a remote unit. Preferably, a control unit assigned to the wearable device, or to the remote unit if applicable, may perform the corresponding calculations and/or evaluations.

Figure 10:
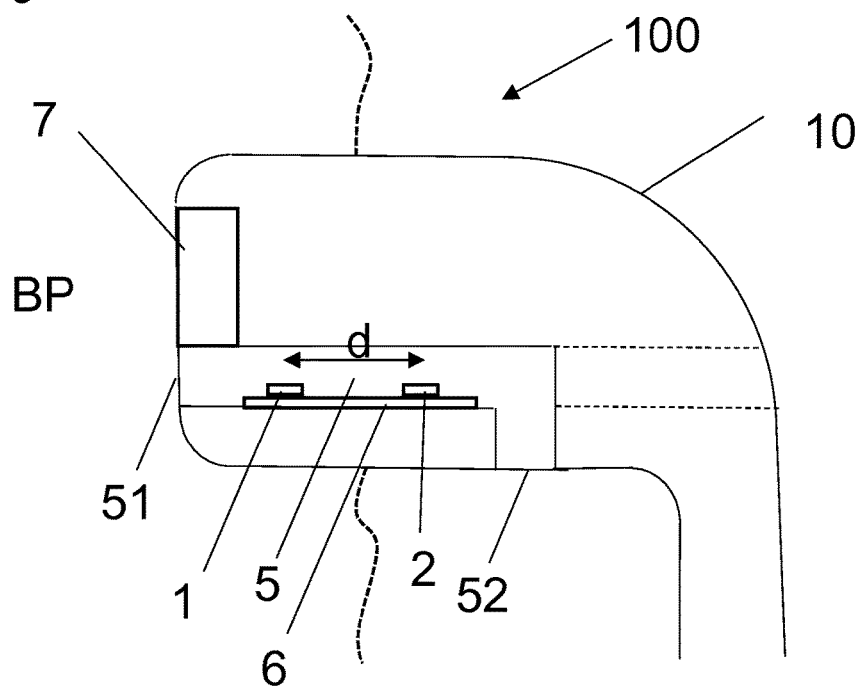
FIG. 10 a cut through an earphone as a wearable electronic device or unit according to an embodiment of the present invention.

FIG. 10 illustrates a cut through an earphone as a wearable electronic device 100 according to an embodiment of the present invention. The earphone comprises a housing 10. A front end of the housing 10 is expected to be inserted into a user's ear which is indicated as body part BP. It is assumed that the body part BP extends to the dashed line during wearing the earphone. A speaker 7 is schematically indicated. A horizontal channel 5 is provided in the housing 10, with an opening 51 at the front end and as such facing the body part BP during wearing. The channel 5 may either be a straight channel as indicated by dashed lines and exits at the opposite end of the ear phone. Or, the channel 5 may have an "L"-shape as shown in FIG. 10 and exits at an opening 52 at a bottom part of the housing 10 which is assumed not to face the ear/body part BP during wearing the earphone.

A circuit board 6 is arranged in the channel 5 with a sensor 1 and a sensor 2 being arranged thereon with a distance d there between, such that the sensors 1 and 2 are exposed to a medium entering the channel 5 by opening 51. With respect to the determination of a flux by means of the two sensors 1 and 2 and all other aspects, it is referred to the description of FIGS. 7 and 9. Again, the determined flux may as such be output and e.g. displayed, or may preferably be evaluated as to if the earphone is plugged into a user ear or not.

The invention claimed is:

1. A wearable electronic device, comprising
a first sensor providing a first sensor signal, which first sensor is a temperature sensor or a humidity sensor,
a second sensor providing a second sensor signal, which second sensor is a temperature sensor or a humidity sensor,
wherein the first sensor and the second sensor are of the same type,
a control unit configured to determine based on the first sensor signal and the second sensor signal if the device is worn by a user, and configured to provide an output signal indicative of a result of the determination,
a common channel including at least one opening, the at least one opening facing a body part of the user when the device is worn by a user, and
wherein the first sensor is arranged in the common channel at a first distance from the at least one opening and the second sensor is arranged in the common channel in spatial series with the first sensor, at a second distance from the at least one opening, the first distance being less than the second distance, the first and second sensors and the common channel being so configured and arranged that the first and second sensors sense an air volume propagated in the common channel and measure a heat flux or humidity flux determined as a difference between the first sensor signal and the second sensor signal.

2. A wearable electronic device according to claim 1, wherein the first sensor is arranged facing a body part of a user when the device is worn by the user, and wherein the second sensor is exposed to ambient air when the device is worn by a user.

3. A wearable electronic device according to claim 1, wherein the first sensor and the second sensor are located on opposite sides of the device.

4. A wearable electronic device according to claim 1, wherein the control unit is configured to determine based on a comparison between the first sensor signal and the second sensor signal if the device is worn by a user.

5. A wearable electronic device according to claim 1, wherein the first sensor and the second sensor are arranged on a circuit board.

6. A wearable electronic device according to claim 1, wherein the control unit is configured to determine based on the first sensor signal and the second sensor signal one or more of a heat flux, a relative humidity flux and a sweat rate when the device is worn by a user and is configured to provide a signal indicative of a result of the determination.

7. A wearable electronic device according to claim 6, wherein the control unit is configured to supply the signal to a display of the device for displaying the result of the determination.

8. A wearable electronic device according to claim 1, wherein the common channel is one of a straight channel, an "S"-formed channel, or an "L"-formed channel.

9. A wearable electronic device according to claim 5, wherein the circuit board is arranged between a first housing part of the device and a second housing part of the device, wherein at least a portion of the common channel is formed by a recess in one of the first and the second housing part and wherein a portion of the circuit board containing the sensor and the other sensor faces the recess.

10. A wearable electronic device according to claim 1, further comprising an earphone, wherein the common channel is provided in a housing of the earphone.

11. A wearable electronic device according to claim 1, wherein the wearable electronic device further includes one of:
    a hearing aid;
    an earphone;
    a headphone;
    a watch;
    glasses;
    a fitness wearable;
    a safety wearable;
    a medical wearable; or
    a piece of clothing.

12. A wearable electronic device according to claim 1, comprising
    a wearable unit including the first and second sensors, and
    a remote unit from the wearable unit, the remote unit including the control unit,
    wherein the wearable unit and the remote unit are connected by means of a wireless or a wired interface,
    and wherein the wearable unit is an earphone or a headphone, and the remote unit is a mobile phone, a tablet computer, or a portable computer.

13. A wearable electronic device according to claim 1, wherein the control unit is configured to trigger an action of the device in response to the output signal.

14. A wearable electronic device according to claim 13, wherein the control unit is configured to trigger at least one of the following actions:
    powering on or powering off one or more of the device, a component thereof, an application thereof;
    switching on or switching off a stand-by mode of one or more of the device, a component thereof, an application thereof;
    stopping or activating logging data from one or more further sensors comprised in the device, in particular wherein the one or more further sensors are medical sensors.

15. A wearable electronic device according to claim 13, wherein the device comprises an earphone or a headphone, and
wherein, if the result of the determination is that the earphone or the headphone is no longer worn by a user, the control unit is configured to one or more of
    pause or stop an active audio component or application,
    switch an active audio component or application to an audio output different from the earphone or headphone respectively,
wherein the wearable unit includes the first and second sensors,
wherein a remote unit from the wearable unit comprises the control unit,
wherein the wearable unit and the remote unit are connected by means of a wireless or a wired interface, and
wherein the different audio output is a speaker of the remote unit.

16. A wearable electronic device according to claim 13, wherein the device comprises glasses or a watch, and wherein, if the result of the determination is that the glasses or watch is no longer worn by a user, the control unit is configured to one or more of
    pause or stop an active video component or application,
    switch an active video component or application to video output different from the glasses or watch respectively,
wherein the wearable unit includes the first and second sensors,
wherein a unit remote from the wearable unit comprises the control unit,
wherein the wearable unit and the remote unit are connected by means of a wireless or a wired interface, and
wherein the different video output is a display of the remote unit.

17. A wearable electronic device according to claim 13, wherein the device comprises an earphone or a headphone, and
wherein the control unit is configured to mute a microphone of the device in case the result of the determination is that the earphone or headphone respectively is no longer worn by a user,
wherein the wearable unit includes the first and second sensors,
wherein a remote unit from the wearable unit comprises the control unit,
wherein the wearable unit and the remote unit are connected by means of a wireless or a wired interface,
and wherein the microphone is arranged in the remote unit.

18. A wearable electronic device according to claim 13, wherein the device comprises a safety or a medical wearable, and wherein the control unit is configured to generate an alert in case the result of the determination is that the safety or medical wearable respectively is no longer worn by a user.

19. A wearable electronic device according to claim 1, further comprising
    a housing and attachment means for attaching the housing to a body part of a user for wearing the device,
    wherein the sensors are arranged either on or in the housing or on or in the attachment means,
    and wherein the control unit is arranged in the housing.

20. A method for determining if a wearable electronic device is worn by a user, comprising
    i) sensing a first temperature using a first temperature sensor or a first humidity using a first humidity sensor,
    ii) further sensing a second temperature using a second temperature sensor or a second humidity using a second humidity sensor, wherein sensing and further sensing are done by sensors of the same type,
    iii) determining, based on the first temperature and the second temperature or the first humidity and the second humidity, if the wearable electronic device is worn by the user, and iv) providing an output signal indicative of a result of the determination,
wherein the wearable electronic device comprises a common channel including at least one opening, the at least one opening facing a body part of the user when the device is worn by the user, and wherein the first sensor is arranged in the common channel at a first distance from the at least one opening and the second sensor is arranged in the common channel in spatial series with the first sensor at a second distance from the at least one opening, the first distance being less than the second distance, the first and second sensors and the common channel being so configured and arranged that the first and second sensors sense an air volume propagated in the common channel and measure a heat flux or humidity flux determined as a difference between the first sensor signal and the second sensor signal.

* * * * *